United States Patent
Davis et al.

(10) Patent No.: US 8,707,963 B2
(45) Date of Patent: Apr. 29, 2014

(54) METHOD FOR PERFORMING IMPLANT SURGERY

(75) Inventors: Todd O. Davis, Leesburg, IN (US); Charles David Fargason, Jr., Houston, TX (US); Onkarr Singh Narula, San Francisco, CA (US); Craig Kessler, New York, NY (US); Jon C. Serbousek, Winona Lake, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 244 days.

(21) Appl. No.: 13/204,192

(22) Filed: Aug. 5, 2011

(65) Prior Publication Data

US 2013/0034838 A1 Feb. 7, 2013

(51) Int. Cl.
*A61B 19/00* (2006.01)

(52) U.S. Cl.
USPC .......................................................... 128/898

(58) Field of Classification Search
USPC ......................................... 128/898; 434/277
See application file for complete search history.

(56) References Cited

U.S. PATENT DOCUMENTS

| | | |
|---|---|---|
| 6,658,322 B1 | 12/2003 | Frederick et al. |
| 7,490,046 B1 | 2/2009 | Wyatt |
| 7,747,406 B2 | 6/2010 | Boing et al. |
| 7,853,470 B2 | 12/2010 | Sonnleithner et al. |
| 2002/0004726 A1 | 1/2002 | Donda et al. |
| 2006/0031109 A1 | 2/2006 | LaRue et al. |
| 2006/0080138 A1 | 4/2006 | Clark |
| 2007/0083286 A1 | 4/2007 | Kobayashi |
| 2008/0183540 A1 | 7/2008 | Lewis |
| 2009/0076878 A1 | 3/2009 | Woerner et al. |
| 2009/0198550 A1 | 8/2009 | Brown et al. |
| 2010/0030571 A1 | 2/2010 | Jones et al. |
| 2010/0306009 A1 | 12/2010 | Wei et al. |
| 2011/0112877 A1 | 5/2011 | Govind et al. |

OTHER PUBLICATIONS

"Maxim® The Complete Knee System, Complete Knee System Primary/Posterior Stabilized Surgical Technique", Brochure, © 1994 Biomet, Inc., 21 pages.

"Microplasty® Elite Knee Instrumentation, Optimized for femoral and tibial preparation when using a minimally invasive approach", Brochure, © 2011 Biomet, Inc., http://www.biomet.com, orthopedics/ productDetail.cfm, 2 pages.

"Microplasty® Elite Total Knee Instrumentation, Surgical Technique, Vanguard® Complete Knee System", Brochure, © 2010-2011 Biomet Orthopedics, biomet.com, Form No. BOI0428.1, REV061511, 76 pages.

"Microplasty® Total Knee Instrumentation, Surgical Technique, Vanguard® Complete Knee System", Brochure, © 2010-2011 Biomet Orthopedics, biomet.com, Form No. BOI0429.1, REV061511, 60 pages.

(Continued)

*Primary Examiner* — Howie Matthews
(74) *Attorney, Agent, or Firm* — Harness, Dickey (57) ABSTRACT

The joint implant manufacturer obtains and compiles surgeon-specific surgical and supply preference information in relation to a supplied joint implant prior to surgery. The manufacturer designates and trains at least one surgical team member using the surgeon-specific preference information and then supplies the service of the surgical team member(s) together with the supplied joint implant and supplies. The surgical team member(s) perform surgical procedures on the patient to assist the surgeon in removing a defective joint and replacing it with the supplied implant in accordance with the surgeon's surgical preferences.

30 Claims, 9 Drawing Sheets

(56) References Cited

OTHER PUBLICATIONS

"Premier™ Total Knee Instrumentation, Surgical Technique, Vanguard® Complete Knee System", Brochure, © 2010-2011 Biomet Orthopedics, biomet.com, Form No. BOI0427.1, REV061511, 64 pages.

"Signature™ Personalized Patient Care*, Surgical Technique Addendum to the Vanguard® Complete Knee System", Brochure, © 2011 Biomet Orthopedics, www.biomet.com, Form No. BOI0376.1, REV051509, 12 pages.

http://www.vantageoutsourcing.com "Vantage Outsourcing Making quality eye care easier, more affordable and more profitable." Aug. 7, 2011 (printed with permission Nov. 15, 2011).

| | | | | |
|---|---|---|---|---|
| 220 → | Surgeon's Name [Surgeon ID] | | | |
| 222 → | Product | Steps [preference] | | |
| | Hip A | step 1 | step 2 [pref] | step 3 [pref] | step 4 |
| | Hip B | step 2 [pref] | step 2 | step 3a [pref] | step 4a |
| | Knee A | step 1 [pref] | step 2 [pref] | step 3 [pref] | step 4 [pref] |
| | Knee B | step 1 | step 2 [pref] | step 3 | step 4 [pref] |
| 224 → | General Preferences | | | |

METHOD FOR PERFORMING IMPLANT SURGERY

FIELD

The present disclosure relates generally to orthopedic implant surgery and joint prostheses installation techniques. More particularly the disclosure relates to methods for improving orthopedic implant procedures by providing surgical team members with unique training based on particular surgeon preferences.

BACKGROUND

Thousands of persons every year undergo surgery to replace a diseased or damaged joint with a prosthesis. That one can have a diseased or damaged joint, such as a hip or knee, removed and replaced on one day, and then be up and walking the same day, seems a miracle to the casual observer; yet it happens every day. This miracle is a testament to the combined ingenuity of the prosthesis engineers and the skill of the orthopedic surgeons and their surgical team. Working together, prosthesis engineers and orthopedic surgeons continually improve their craft every year, developing new prosthetic devices, new instruments to install them, and new surgical procedures. It is an evolving science and an art form.

To be sure, orthopedic implant surgery, such as replacement of a human joint with a prosthetic joint, is a highly specialized and demandingly complex process. An orthopedic surgeon will typically learn his or her craft during a fellowship under the tutorage of a master surgeon. The new surgeon will then go on to become a master surgeon as well, further improving the surgical craft and passing that knowledge on to others.

The basic procedures for replacing a joint with a prosthesis generally follow an established workflow that is dictated by the physical geometry of the prosthesis and the human body. However, because no two patients are exactly alike, no two joint replacement surgeries will be exactly alike. Thus each time the surgeon opens up the patient with the first scalpel cut, the surgeon must be prepared to make countless in situ decisions: cut 2 mm deeper here, abrade bone spurs there, use antibiotic-infused cement, don't use antibiotic-infused cement, the list goes on and on. In short, the surgeon must make countless split second decisions and must be prepared to improvise based on what he or she finds once inside the patient.

In many respects the orthopedic surgeon is like a professional basketball player. His moves are highly skilled, the path to the goal involves many judgment calls and split decisions, and most importantly, the surgeon works as part of a team. To be successful each member of the surgical team must perform his or her job with precision, always mindful of the surgical objective, and always mindful of the surgeon's surgical preferences. If the surgeon needs a wider opening in which to insert the reamer, the surgical team member must instinctively know to pull a bit tighter on the number 6 retractor, for example. If the surgeon likes to assess the position of a cutting block before making an important cut, the surgical team member anticipates this and hands the surgeon the fluoroscopic instrument, if that is the surgeon's preference. There are of course countless variations. A different surgeon might prefer to make a longer cut to ease insertion of the reamer; or might prefer to position the cutting block by manually sensing its position with the fingers.

Quite simply, a well-trained, well-rehearsed surgical team who understand the procedures and know the surgeon's preferences will allow the surgeon to replace a diseased or damaged joint with a prosthesis in the shortest possible time. Making the surgeon more efficient saves cost, allows the surgeon to perform more surgeries per day, and quite importantly, it shortens the length of time the patient lies in the operating room with an open wound exposed to the elements.

While the well-trained, well-rehearsed surgical team is certainly the goal, there is a large practical problem that must be overcome. Hospitals typically supply the surgical nurses and these nurses may be assigned to work for a large number of different surgeons, including surgeons with other orthopedic practices. There has heretofore been no practical way for hospital-supplied surgical nurses to efficiently and effectively learn individual surgeon preferences, and thus it is rare that any given hospital-supplied surgical team will ever approach optimal efficiency.

SUMMARY

The method for performing orthopedic implant surgery disclosed here fundamentally changes how such surgery is performed, by changing how the surgical team assisting the surgeon is deployed. In accordance with the method, the manufacturer or implant supplier that supplies a joint implant or prosthesis to a surgeon for implantation into a patient obtains and compiles information from the surgeon prior to surgery about the surgeon's preferences in relation to the supplied joint implant. The manufacturer or supplier designates and trains a surgical team in the manner of implanting the supplied joint implant in accordance with the surgeon's preferences. Finally, the manufacturer or supplier supplies the services of the surgical team together with the supplied joint implant.

The surgical team member, trained and supplied by the manufacturer or supplier, then performs procedures on the patient to assist the surgeon in implantation of the supplied implant, in accordance with the surgeon's preferences learned during the training.

In this way, the manufacturer or supplier supplies a bundled product: the prosthetic implant with instruments and supplies used to install it, together with a trained, scheduled surgical team, who provide surgical services based on the individual surgeon's surgical preferences. This results in a much more efficient prosthetic implant surgery. The surgeon can perform more surgeries per day and with the important benefit that the patient's surgical wound is open for a far shorter time, reducing the risk of post-operative complications.

From the patient's point of view, the surgical process can generally be subdivided into three stages. The pre-operative stage begins when the patient clears registration and ends when the patient is wheeled into the operating room. The intra-operative stage begins when the patient is wheeled into the operating room and ends when the patient is wheeled out of the operating room. Although the patient undergoes physical manipulation in all three stages, the implant is actually installed during this intra-operative stage. The post-operative stage begins when the patient is wheeled out of the operating room or is released from the post anesthesia care unit and ends when the patient is discharged from the hospital. The method for performing orthopedic surgery disclosed herein impacts how the intra-operative surgical team is deployed, and optionally how the pre-operative and post-operative teams are deployed as well.

As used herein, the term "surgical team" means the group of skilled individuals who assist the surgeon during the intra-operative stage. Members of the surgical team would thus include the circulator nurse or circulating nurse, whose overall role is to ensure the operating room is running smoothly and according to protocols; the scrub technician or surgery technician, whose role is to assist the surgeon by handing off tools, instruments, trials, and implants, and assisting in holding tools; the physician's assistant or nurse practitioner, whose role is to assist the surgeon during the surgery and to close the wound after capsule closure, if called upon to do so; the anesthesia assistant or CRNA, whose role is to assist the anesthesiologist in managing patient care during the surgery; and the orthopedic assistant, whose role is to help keep the operating room clean and to help turn the room over in preparation for the next patient.

As used herein, the term "pre-operative team" means the group of skilled individuals who assist during the pre-operative stage; members of the pre-operative team would thus include the pre-operative nurses who prepare the patient for surgery. As used herein, the term "post-operative team" means the group of skilled individuals who provide health care services to the patient during the post-operative stage, and thereafter to promote the healing process; members of the post-operative team would thus include recovery room nurses who ensure the patient recovers from the anesthesia used during surgery (in the case where the post-operative stage begins when the patient is wheeled out of the operating room), floor nurses to ensure the post-operative orders are being followed and to take care of patent needs and wants, and physical therapists and physical therapist assistants who ensure the patients are actively following the exercise protocols to ensure rehabilitation.

In addition to these teams, the orthopedic surgery will also typically utilize a site manager responsible for the overall operation of the program and the surgical team(s). It will be understood that the foregoing staff and roles are general descriptions and will vary given the personality, location and size of the hospital and surgeon(s). Additional roles, or conversely reduced surgical team sizes are possible given particular circumstances. Thus the foregoing descriptions are intended to be exemplary and not exhaustive of all possible roles and team member assignments.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1A:
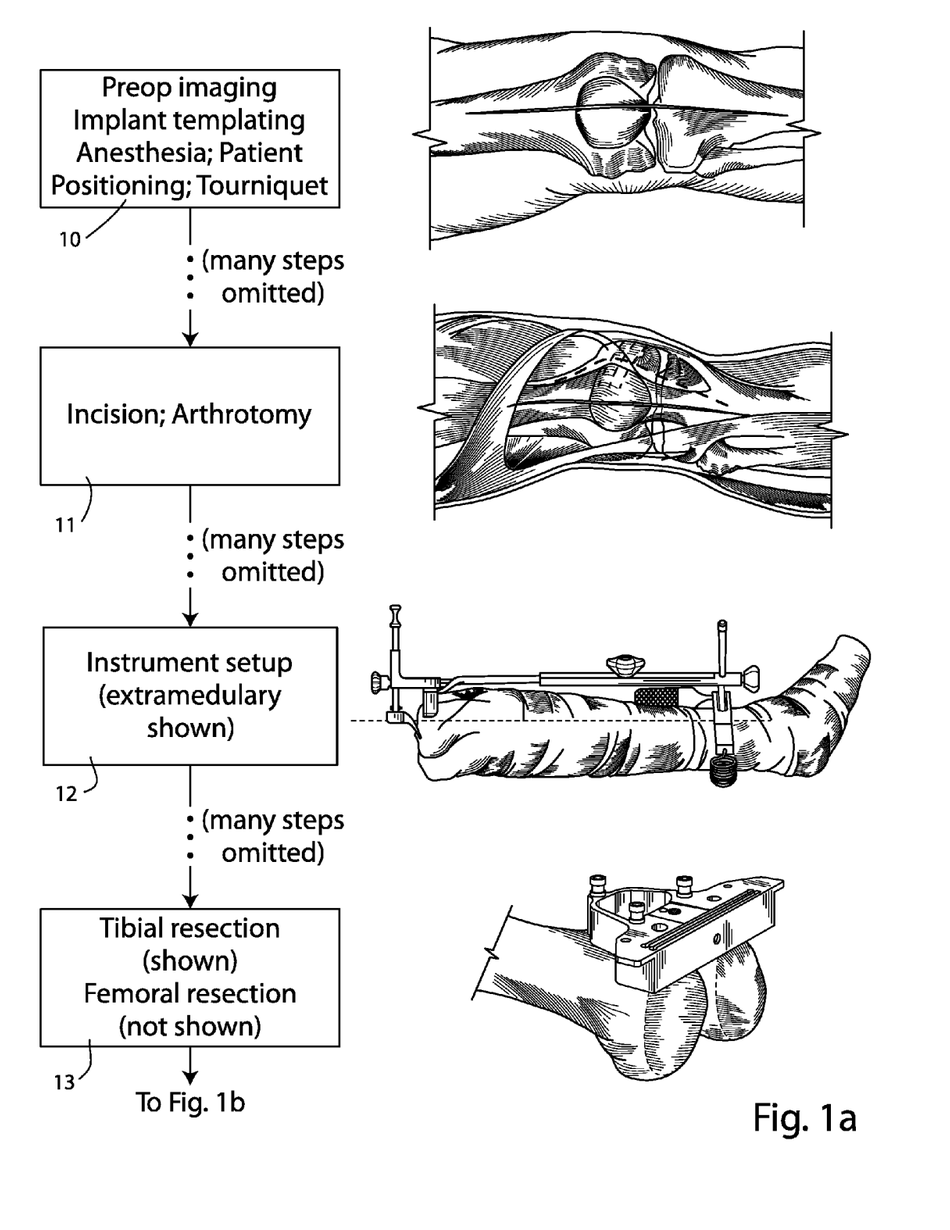
FIGS. 1a-1c comprise a flowchart showing an exemplary orthopedic implant surgical procedure, useful in understanding the context in which the method is performed.
Figure 1B:
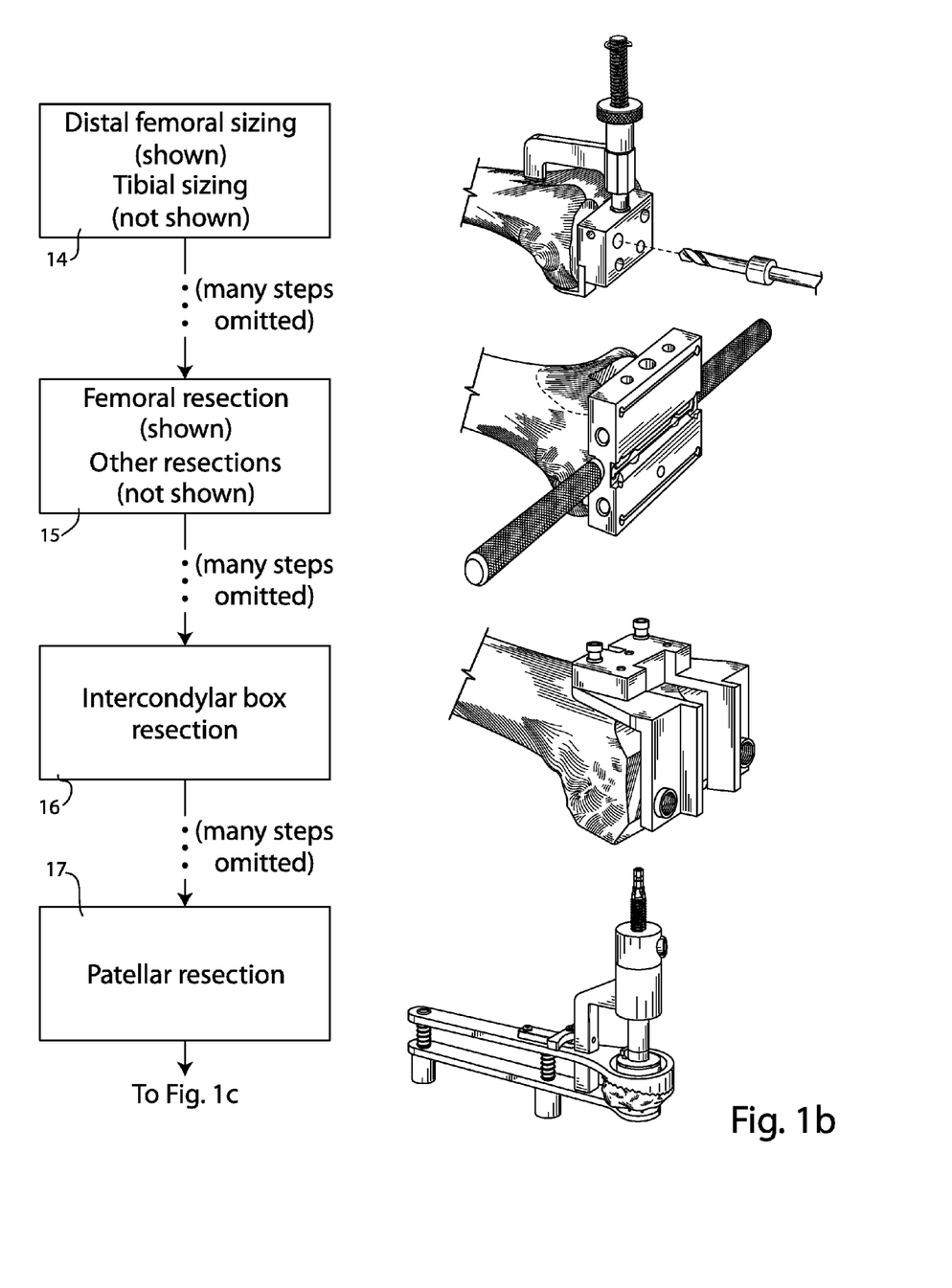
Figure 1C:
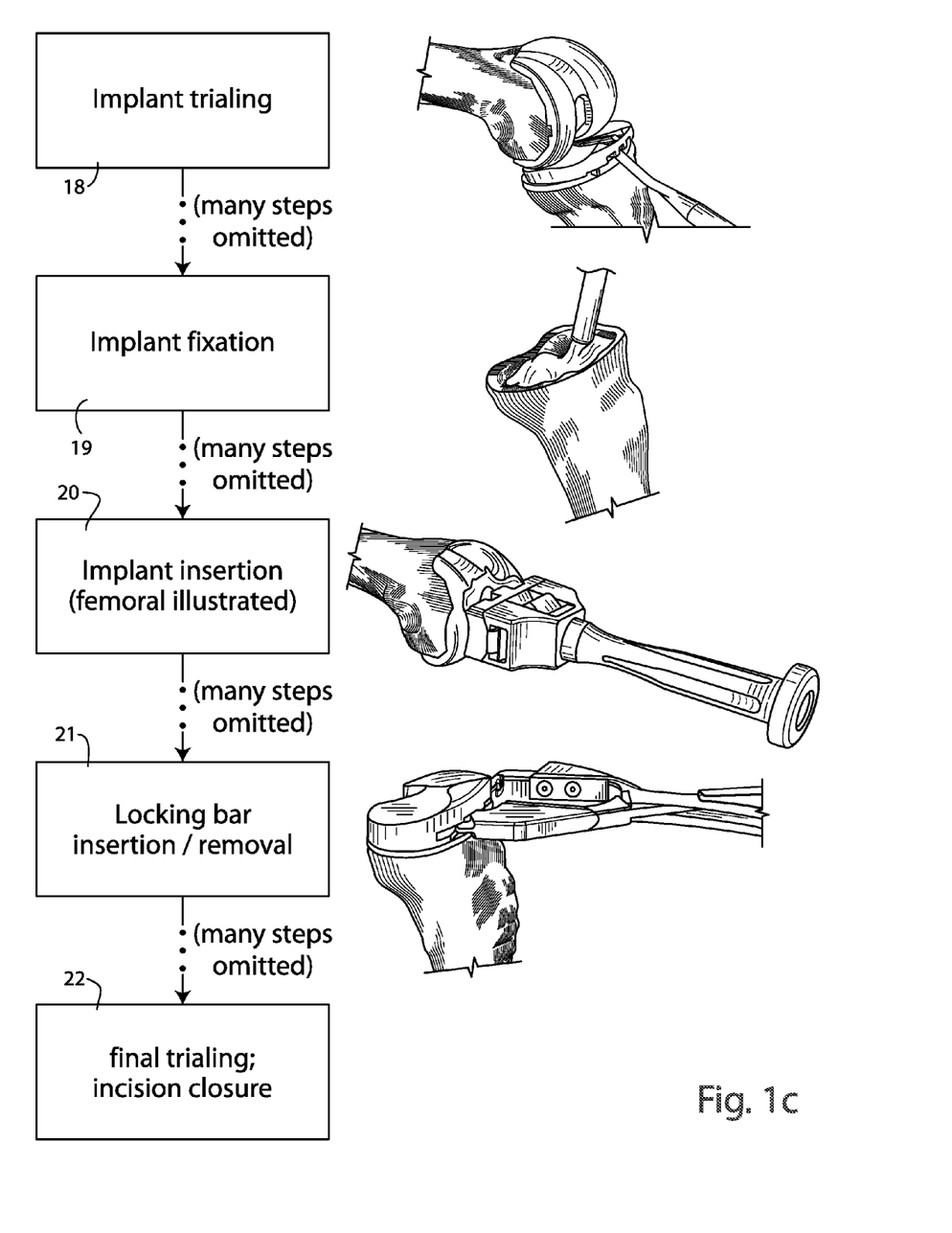

Before explaining the method for performing orthopedic implant surgery in detail, a basic overview of an exemplary orthopedic implant surgery will be presented. Shown in FIGS. 1a-1c are representative examples of a few of the basic steps employed in an exemplary knee replacement surgery. It will of course be appreciated that FIGS. 1a-1c are intended merely to give a general overview of how orthopedic surgery is conducted. There are numerous variations, depending on the style and technology of the prosthesis used, the age and condition of the patient, the nature of the defect or disease precipitating the surgery, and numerous permutations based on surgeon preferences. Many details have been omitted from FIGS. 1a-1c.

As illustrated in FIGS. 1a-1c, a basic knee replacement surgery involves opening the joint by incision, attaching guides to the tibia and femur, resecting (cutting away) portions of the bone to accommodate the mounting surfaces of the prosthetic implant, attaching guides and resecting the patella, attaching the implant and closing the wound. Typically, the surgeon will operate on one bone at a time, attaching guides and resecting that bone before moving on to the next. However workflows do differ.

Referring to FIG. 1a, at step 10, preoperative imaging using X-rays or other imaging devices determines the size and positioning of the implant. Implant templates may be used for this purpose. The patient is then anesthetized and a tourniquet is applied. The patient is covered with a surgical drape that exposes the surgical site and the patient's skin is painted with a disinfectant such as iodine or chlorhexadine.

Next the surgeon determines where to make the incision and draws the incision line on the patient's skin using a sterile marker. Often additional guide marks referenced to anatomical features such as the trochanter are drawn to help locate the incision line. Then, at step 11, the surgeon cuts through the epidermal and dermal layers along the incision line using a scalpel, while surgical team members pull back the incised layers using curved retractors to better expose the layers beneath. Once exposed the surgeon cuts the joint, a process called arthrotomy, so that the exposed tibia, femur and patella can be individually operated upon.

Before making any bone cuts the surgeon uses various guide instruments as illustrated at step 12 to assist in accurately positioning and attaching a resection block, used to guide each saw cut. The illustrated guide featured in step 12 is attached extramedulary, that is, on the outside of the leg. Some surgeons use a different procedure and prefer an intermedulary guide, which must be attached inside the bone itself. The guide featured at step 12 is designed to aid in locating the tibial resection block against the anterior tibia. Other guides are used to attach other resection blocks; these have been omitted from FIGS. 1*a*-1*c* to abbreviate the explanation.

After a resection block has been attached, as with pins driven into the bone, resection is performed using a specialized motorized saw. Step 13 illustrates the resection block in place for the distal femoral resection. Note the slots along the top of the resection block to guide the saw blade in making the cut along the dashed lines.

Refer next to FIG. 1*b*. Once the resections have been made, the surgeon next performs the sizing operation, as illustrated at step 14. A sizing instrument is attached, as illustrated. Featured at step 14 is the sizing instrument for the distal femoral region. It is attached to the posterior condyle.

It will be appreciated that the resection of each bone involves entirely different geometry, thus dictating entirely different guides, resection blocks and sizing instruments. For illustration purposes, shown at step 15 is the femoral resection block. Shown at step 16 is an intercondylar box resection block that may be used to work the intercondylar area.

To accommodate the geometry of the implant, the surgeon reworks the patella by using an instrument such as a mill reamer. Calipers measure the overall patella height; a mill guide is clamped to the patella and then a motorized reamer is applied to remove a portion of the patella. The mill reamer is illustrated at step 17.

Refer now to FIG. 1*c*. Prior to installing the implant, the surgeon will first perform implant trialing, as depicted at step 18. This entails placing different test implants into position on the respective bones, trying out different sizes to ensure the finished joint will function properly and give the patient the desired degrees of freedom of movement.

After the surgeon is satisfied with his or her implant size selection, the implant is fixed in a permanent location by using screws, cement or other bonding agents. Step 19 illustrates how adhesive bone cement would be applied. The resected surfaces are thoroughly cleaned and the cement is mixed in exact proportion and applied in a semi-liquid state to the bone surface. Some surgeons also prefer to apply a thin layer of cement to the underside of the implant as well.

As shown at step 20, the implant is finally inserted into place, using a specially designed instrument. Often a hammer is used to impact the implant into its proper position. Shown at step 20 is the femoral implant being installed in this fashion.

The typical knee implant may include a bearing material, such as a polyethelene bearing that is inserted on the tibial baseplate. As illustrated at step 21, the bearing is held in place with a locking bar, inserted into the medial side of the polyethelene bearing as far as it will go. A special instrument is used to install the locking bar. The same instrument would be used to remove the locking bar if necessary.

Finally, after all components of the implant are installed and working properly, the surgeon performs final trialing of the joint to ensure it achieves the desired range of movement and to ensure that the patient's leg is of proper length. Once satisfied, the incision is closed and the patient is moved to the recovery room.

As will be appreciated each of the illustrated steps (and the many that were not illustrated) involve multiple substeps. In practice, the substeps encompass a wide range of different surgical procedures as dictated by the prosthesis geometry and importantly by surgeon preference. Thus, for illustration purposes, FIGS. 1*a*-1*c* have shown only a very few of the many surgeon-specific preference associated with each of the illustrated steps. It will be understood that these illustrated preferences are merely examples. There are many more.

Although a knee replacement surgery has been illustrated in FIGS. 1*a*-1*c*, it will be understood that a comparable flowchart also exists for hip replacement surgery, and for other orthopedic surgeries as well. Although some surgeons specialize on a particular type of surgery, many orthopedic surgeons today perform a range of different surgical procedures on numerous joints of the human body. Hip replacement and knee replacement represent the two largest categories. Thus, a typical orthopedic surgeon may likely perform both hip surgeries and knee surgeries on any given day. It is customary for the surgeon to schedule new prosthetic implant cases first, thereby leaving the end of the day open to perform revisions to existing implants. Revision work is typically scheduled last because there is more variability and the surgeon does not know what types of complications he or she may encounter when the existing condition is exposed.

Given that the surgeon may typically perform primary hip surgeries, primary knee surgeries, hip or knee revisions and other surgeries during a single day, the surgical team needs to be well-versed in the full range of possible procedures. The present method for performing implant surgery improves upon conventional practice by designating, training and providing these surgical team members in a unique way.

Figure 2:
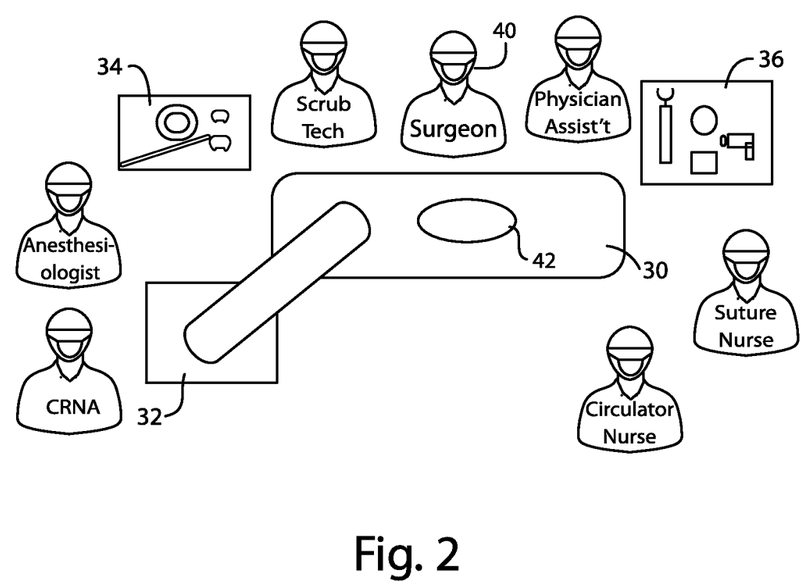
FIG. 2 is a plan view of an exemplary orthopedic operating room.

Of course, operating room layouts and staffing may differ, but FIG. 2 shows one exemplary operating room layout, illustrating the operating table 30, X-ray machine 32, and trays of surgical implements 34 and 36. The surgeon 40 stands adjacent to the opening in the surgical drape 42 and is surrounded by the surgical team members, as illustrated. Although the complement of surgical team members may differ, a typical operating room will employ a plurality of members who each fill different roles and thus perform different functions. The following is provided by way of example of some of the different possible roles.

Scrub technicians have direct contact with the surgical team and the patient during surgery. They stand alongside the surgeon, handing the surgeon the required instruments and performing other operations upon the patient as required by the surgeon, including using retractor tools to retract tissue while the surgeon accesses more deeply located structures within the patient's body. Scrub technicians may also assist in rinsing or cleaning the operating tools as soon as the surgeon puts them down and may also assist in applying suction to remove bodily fluids from within the wound.

Physician's Assistants or Nurse Practitioners assist the surgeon by performing a variety of surgical tasks, including assisting the surgeon in closing the wound after surgery, applying sutures as required.

Anesthesiologist Assistants or Certified Registered Nurse Anesthesiologists (CRNA) may also be employed. They assist the anesthesiologist and help ensure the patient is responding well to the general anesthetic.

Circulating nurses assist the surgical team by providing a variety of different coordinating services as needed. For example, if a tool needs to be obtained from the central supply room during surgery, the circulating nurse would see that it is obtained. A circulating nurse or, alternatively, a managing or head nurse, may function to ensure that the operating room is in order and that the staff are all present and in position at the time of surgery.

In a conventional operating room scenario, these surgical nurses are supplied by the hospital. Although skilled, these hospital-provided nurses may have a wide range of other, unrelated duties, including surgical duties unrelated to the orthopedics field. Such nurses may have little or no a priori knowledge or instruction regarding a particular surgeon's surgical preferences.

Implant Manufacturer-Supplied and Trained Surgical Team

Figure 3:
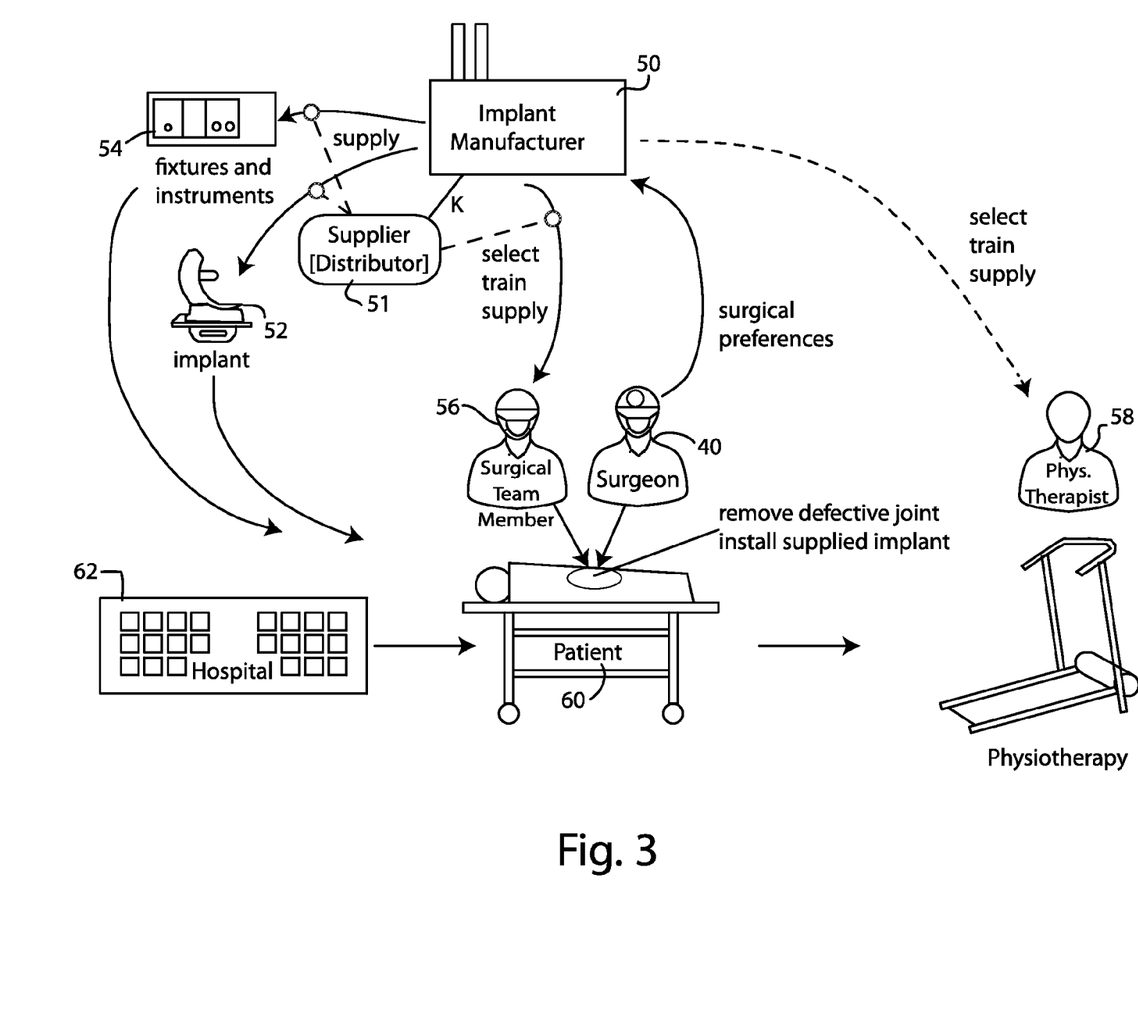
FIG. 3 is a simplified entity relationship diagram showing the interaction among various entities, including surgeon, surgical team member(s) and patient, to implant the orthopedic implant.

In accordance with one preferred embodiment, the method for performing implant surgery improves upon the conventional scenario by bundling the surgical team function with the prosthetic implant, instruments and supplies. In a presently preferred embodiment the implant, instruments and supplies are bundled with surgical team services at one price. Thus, the implant and the surgical team members are both supplied by the implant manufacturer, as illustrated in FIG. 3, or by an implant supplier 51, as depicted by the dashed lines. The implant manufacturer 50 or supplier 51 supplies not only the implant 52 and the accompanying supplies and instruments 54, but also the surgical team 56.

In one embodiment, the implant manufacturer 50 selects, trains and supplies the surgical team based on the individual preferences of the surgeon performing the surgery. In another embodiment, the implant supplier 51 trains and supplies the surgical team, preferably based on the individual preferences of the surgeon. The implant manufacturer 50 and supplier 51 may have a contractual relationship, shown diagrammatically at K, whereby the supplier 51 distributes the manufacturer's prosthetic implants, instruments and supplies and optionally uses information about individual surgeon preferences obtained and compiled by the manufacturer to train the surgical team.

Additionally, if desired, the implant manufacturer 50 or implant supplier may also select, train and supply staff used in pre-operative procedures, and/or in post-operative procedures, such as physiotherapy. Thus, FIG. 3 illustrates the implant manufacturer or implant supplier 51 optionally supplying a post-operative team member, such as the physical therapist 58. The implant manufacturer or implant supplier may also select, train and supply post-operative team members (not shown).

In the illustrated embodiment, the patient 60 enters the hospital 62 or orthopedic clinic (not shown) where the operating room is located. The hospital or clinic remains involved in providing a range of medical services, such as providing and administering drugs such as antibiotics and pain blockers. The hospital or clinic will likewise maintain responsibility for patient administrative functions, including admitting the patient to the hospital, billing the patient and the like. However, unlike the conventional approach, the surgical team members, and optionally other pre-operative and/or post-operative teams, are supplied and trained by the implant manufacturer, or by a supplier in privity with the implant manufacturer. In one presently preferred embodiment, the supplied surgical team members and optional pre-operative and post-operative staff are employees of the implant manufacturer or otherwise contractually controlled by the implant manufacturer.

Given the large number of surgeon-specific preference variations from one surgical procedure to the next, training a staff of surgical team members on the individual surgical preferences of every surgeon across the country, is a daunting task, impossible to reasonably perform without special techniques and specialized technology. To complicate matters, in a presently preferred embodiment, the individual surgical team member candidates are selected from local markets, that is, from localities near a particular hospital or clinic.

Figure 4:
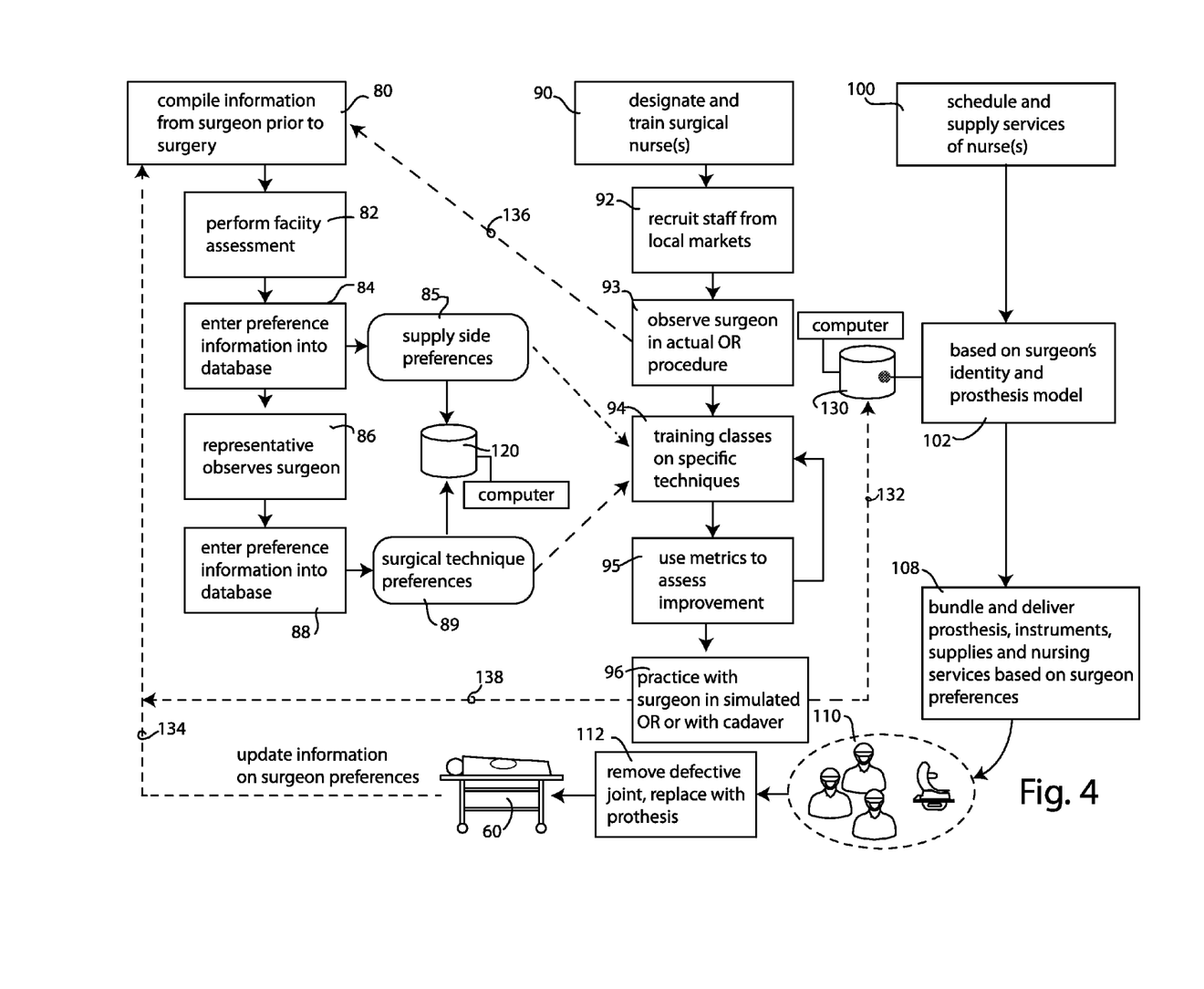
FIG. 4 is a series of interrelated flow diagrams illustrating obtaining, compiling and using surgeon preference information in the training and providing of surgical team member(s) bundled with prosthesis.

To address the demanding training problem, a preferred embodiment follows the process shown in FIG. 4. The process concatenates three interrelated workflows shown generally at 80, 90 and 100. In one preferred embodiment the implant manufacturer performs and/or supervises each of these workflows. The first workflow, beginning at step 80, compiles information from each surgeon prior to surgery. As will be more fully explained, surgeon-specific preferences are compiled and stored in a computer-implemented database that is used to develop training classes geared to teach not only general prosthetic implant techniques, but surgeon-specific preferences. The explanation provided in FIG. 4 focuses on how the training and scheduling function would be performed by the implant manufacturer. The workflows would be essentially the same when performed by an implant supplier.

The next workflow, depicted at 90, describes how the surgical team members are designated and trained by the implant manufacturer. The final workflow 100 depicts how a surgical nursing staff is assembled, scheduled and supplied along with the prosthetics and accompanying instruments and supplies to a particular operating room where the defective joint is removed and replaced with a prosthesis. The details of workflows 80, 90 and 100 will next be described.

As at 82, the first step in compiling surgeon-specific information is to perform a facility assessment. An assessment agent of the manufacturer or supplier visits the hospital or clinic where the operating room is located and gathers information about facility-specific preferences the surgeon may have. These data, referred to as supply side preferences 85, are then entered as preference information into the computer-implemented database 120, as at 84. The objective here is to gather as much surgeon-specific, supply preferences as possible. For example, if the surgeon prefers a certain type of size 8 brown latex gloves, then that information would be gathered and entered. If a surgeon prefers a certain type of instrument, such as a particular style of reamer or saw, that information would likewise be entered into database 120.

In conjunction with gathering supply side preference data, the manufacturer's or supplier's representative also observes the surgeon performing a surgical procedure as at 86 and enters surgical technique preference information 89 into the database 120, as at step 88. Because different surgical procedures may necessarily entail different surgical techniques (hip surgery is different from knee surgery), the representative will endeavor to collect information from as many different types of surgical procedures as he or she is able to observe.

The interrelated workflow processes 90 and 100 afford other opportunities to gather surgeon-specific information, including additional supply side preferences 85 and additional surgical technique preferences 89. This will be described later.

Once the computer-implemented database 120 includes sufficient data to fairly represent the individual surgeon's preferences, the information is used to develop surgeon-specific training as will now be discussed with reference to workflow 90.

The first step in designating and training surgical team members involves recruiting suitable team members from local markets, as at 92. As discussed above, recruiting from local markets is preferred because the trained surgical team members will likely be deployed at hospitals or clinics near where they live. Once a suitable staff has been recruited, they are placed in the observation deck to observe an actual operating room procedure being performed by the surgeon whose preferences they will be trained to accommodate. This is illustrated at step 93. Thereafter, at step 94, training classes are conducted on specific techniques based on the particular surgeon's preferences as stored in database 120. Thus, at step 94, the team members-in-training receive specific instruction on supply side preferences 85 and surgical techniques preferences 89 of that surgeon. The training on specific techniques is tested as at 95 using quantitative metrics designed to assess the trainee's improvement. As illustrated, steps 94 (training) and 95 (testing) are iteratively performed numerous times until the team member-in-training is able to perform all the different techniques with a high degree of skill. Training is conducted both on an individual basis and also on a team basis, so that each team member-in-training has an opportunity to learn each other team member's role, thereby making them aware of the overall process and allowing one to fill in for the other if circumstances warrant. In one embodiment, performance metric data may be gathered for use later during scheduling.

Finally, at step 96, the team members-in-training are assembled and placed into a simulated operating room where they perform their respective tasks, along with the surgeon whose preferences they have now learned. This practice session may be performed using human cadavers or other surgical simulators. Thus, at step 96, the assembled surgical team has an opportunity to practice their newly learned skills with the surgeon whom they will later be assisting.

While the venue for training surgical team members as outlined in workflow 90 can be performed at any convenient location, in many instances it may prove convenient to conduct training classes on specific techniques (step 94) and perform metric testing (step 95) at the implant manufacturer's training facility. Practice with the surgeon in the surgical simulation may also be conducted at the implant manufacturer's facility.

Having now explained how the surgical team members are trained, refer to workflow 100 which illustrates how the trained team members are thereafter deployed on an as-needed basis to assist the particular surgeon in performing joint replacement. In preparation for surgery, at step 102, the surgical team that has been trained in the particular surgeon's preferences and in the prosthesis model being used is identified by accessing database 130, using the surgeon's identity and prosthesis model to query the database.

Database 130 is populated with a list of qualified surgical team members who have successfully completed the training process 90, as illustrated by the dashed line 132, with indicia as to which surgeon's preferences the team has been trained in. If desired a team can be trained to support more than one surgeon, by training that team in the preferences of multiple surgeons. Once the team is selected, the manufacturer or supplier at step 108 bundles and delivers the prosthesis, the instruments and supplies used for installing the prosthesis and the nursing services of the assembled team members to the surgeon or hospital for use on the day of surgery. All of this is based on surgeon preferences.

In effect, instead of merely supplying the implant, instruments and related supplies, the manufacturer includes a service component with the deliverables, as diagrammatically illustrated at 110. Thus, the "product" being delivered comprises a high technology prosthetic implant with a specifically trained surgical nursing staff to assist in installing the implant based on the particular surgeon's preferences. This assembled team, together with the surgeon, thus perform the surgical procedure at 112 by removing the defective joint and replacing with the supplied prosthesis.

If desired, the bundled product comprising implant (and optionally instruments and related supplies), combined with surgical team services may be offered and invoiced at a single bundled price comprising a materials component (implant, instruments, supplies) and a labor component (surgical team services).

At this stage in the explanation, it bears noting that the concatenated interconnected workflows of FIG. 4 afford several opportunities to harvest additional information regarding surgeon preferences. A designated member of the surgical team may be tasked with the responsibility of seeing that any new or previously undiscovered preferences, revealed during the surgery, are compiled into the database 120, as depicted by the dashed feedback line 134. Information about surgeon preferences can also be gathered from steps 93 and 96 during the training workflow as depicted by dashed lines 136 and 138.

Figure 5:
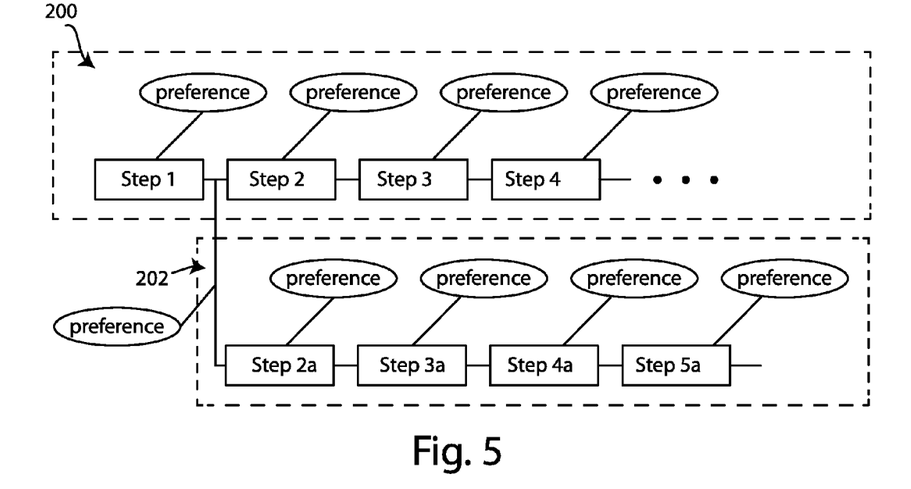
FIG. 5 is a process diagram illustrating a generalized surgical procedure workflow where each step of the workflow may include variation based on individual surgeon preference.

In one embodiment the computer-implemented database 120 that stores surgeon preference information preferably accounts for both supply side preferences 85 and surgical technique preferences 89. Surgical technique preferences are preferably stored on a surgical step-by-step basis. This has been illustrated diagrammatically as the data structure shown in FIG. 5. FIG. 5 shows an exemplary series of surgical steps 200 which may optionally branch into an alternate series of step 202, as illustrated. The data structure for storing these steps is designed to be complete. Each individual step within the series of steps 200 and 202 corresponds to a particular step in the surgical procedure and is stored in the data structure. With reference to FIG. 1, each of the aggregated steps shown there might correspond to a dozen or more individual steps 200 or 202 in FIG. 5. As illustrated, each individual step within the sequence has associated with it a surgeon-specific preference. In actual practice, a given surgeon may or may not have a particular preference for one or more of the steps. In such case, the computer system would simply store a null value for a step where no preference has been entered.

Figure 6:
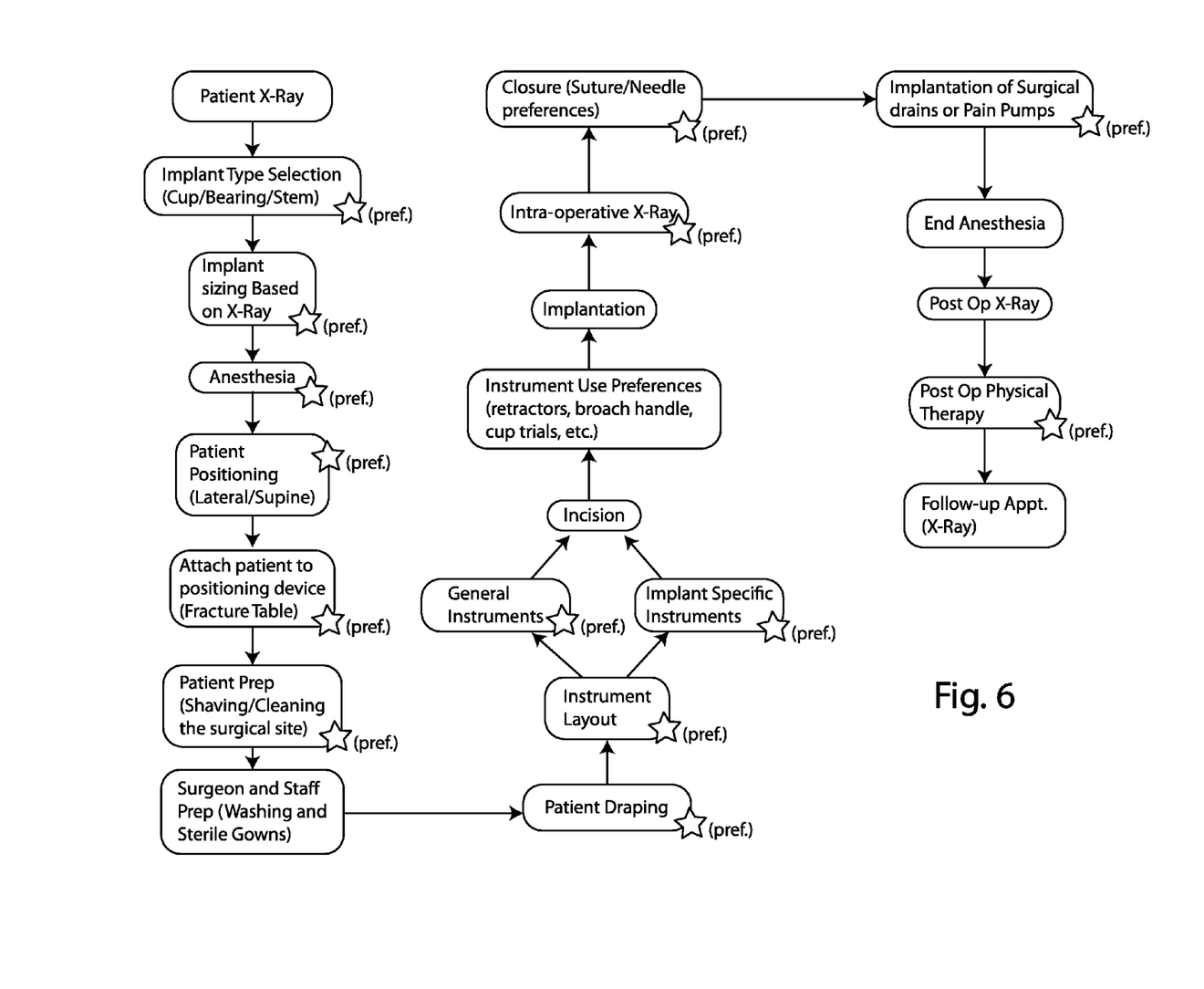
FIG. 6 is a flowchart illustrating the general surgical steps involved in hip replacement surgery.

To better appreciate the complexity and the number of different step-preferences involved refer to FIG. 6 and to Table I below. FIG. 6 shows the general surgical steps involved in hip replacement surgery, where some of the steps have been annotated to highlight those where variation due to surgeon preference is most prevalent. Some of the surgeon preference choices have been indicated in parentheses in the described steps. Table I presents the general surgical steps involved in knee replacement surgery. It will be recalled that knee replacement surgery was featured, in a highly abbreviated fashion, in FIG. 1. The left-most column of Table I sequentially lists each surgical step; the remaining columns show examples of different surgeon preferences for the associated step.

TABLE 1

| Surgical Steps for Example Knee Prosthesis | Preference A | Preference B | Preference C | Preference D | Preference E | Preference F |
|---|---|---|---|---|---|---|
| preop imaging | MRI (Signature) | x-ray (standard) | | | | |
| preop implant templating | Signature planner | digital x-ray templating | acetate x-ray templates | | | |
| anesthesia | general | epidural | | | | |
| patient positioning | | | | | | |

TABLE 1-continued

| Surgical Steps for Example Knee Prosthesis | Preference A | Preference B | Preference C | Preference D | Preference E | Preference F |
|---|---|---|---|---|---|---|
| leg positioning | boot | sandbag | | | | |
| tourniquet | with tourniquet | without tourniquet | | | | |
| incision | midline incision | | | | | |
| arthrotomy | standard medial parapatellar | mini medial parapatellar | mid vastus | sub vastus | | |
| distal femoral resection instrument | Microplasty instrument | Premier instrument | Microplasty Elite instrument | EM instrument | Signature | |
| distal femoral angle | 4 degrees | 5 degrees | 6 degrees | 7 degrees | other | |
| distal femoral resection depth | 8 mm | 9 mm | 11 mm | 12 mm | other | |
| distal femoral resction guide | with handles | without handles | pinned with drills | pinned with bone nails | | |
| distal femoral resection | sawblade length | sawblade thickness | recut | | | |
| AP sizing instrument | Microplasty instrument | Premier instrument | Microplasty Elite instrument | anterior referencing | Signature | |
| femoral rotation reference | posterior condyles | epicondylar axis | AP axis | Signature | | |
| femoral cutting block | Slidex block | Premier block | check with feeler blade | downsize/ recut | handles or not | |
| tibial cut alignment reference | EM | IM | Signature | | | |
| tibial cut instrument | Microplasty instrument | Premier instrument | Microplasty Elite instrument | IM instrument | | |
| tibial cutting block | anatomic | universal | captured slot | surface | | |
| tibial cut depth | stylus | eyeball | Signature | | | |
| tibial cut posterior slope | none | 0-3 degrees | 3-7 degrees | other | | |
| tibial cut v/v slope | none | | | | | |
| tibial sizing instrument | Microplasty instrument | Premier instrument | Signature | | | |
| tibial rotation | medial third of tubercle | ROM method | Signature | | | |
| tibial stem | I-beam | cruciate | Microplasty | offset | long stem | |
| tibial stem prep | Microplasty instrument | Premier instrument | mark and punch | | | |
| patella resection | mill | saw guide | freehand | unresurfaced | | |
| patella sizing | 28 | 31 | 34 | 37 | 40 | other |
| patella peg configuration | single peg | three peg | | | | |
| trialing | Microplasty instrument | Premier instrument | | | | |
| implant fixation | cementless | cemented | | | | |
| mixing cement | vacuum mixing | bowl mix | antibiotics | high viscosity/ medium viscosity | cement brand | |
| implanting components | impactor fixed to femoral | impactor fixed to tray | location of cement - bone, component, both | order of implantation | assembly of locking bar | |
| knee injection | | | | | | |
| clean joint | remove cement debris | lavage joint | | | | |
| final trialing | assess patella tracking | assess soft tissue | select final bearing - CR, CRL, As | perform final soft tissue releases if necessary | | |
| incision closure | close in ext. vs. flexion | staples vs. suture | drain vs. no drain | | | |
| retractors | retractor design | retractor positioning | | | | |
| postop pain management | | | | | | |
| rehab protocol | | | | | | |

From the foregoing it will now be appreciated that, when viewed at the industry level, a complex orthopedic surgery will entail potentially hundreds of surgical steps, with many optional branches, and many, many permutations based on individual surgeon preferences, resulting in an enormous database. The data structure illustrated in FIG. 5 is designed to store this information. Because the surgeon may potentially perform a variety of different joint replacements in a given day, such as hip replacements, knee replacements and so forth, the data structure of FIG. 5 is replicated for each different type of procedure, and for each different type of implant used for each procedure.

Figure 7:
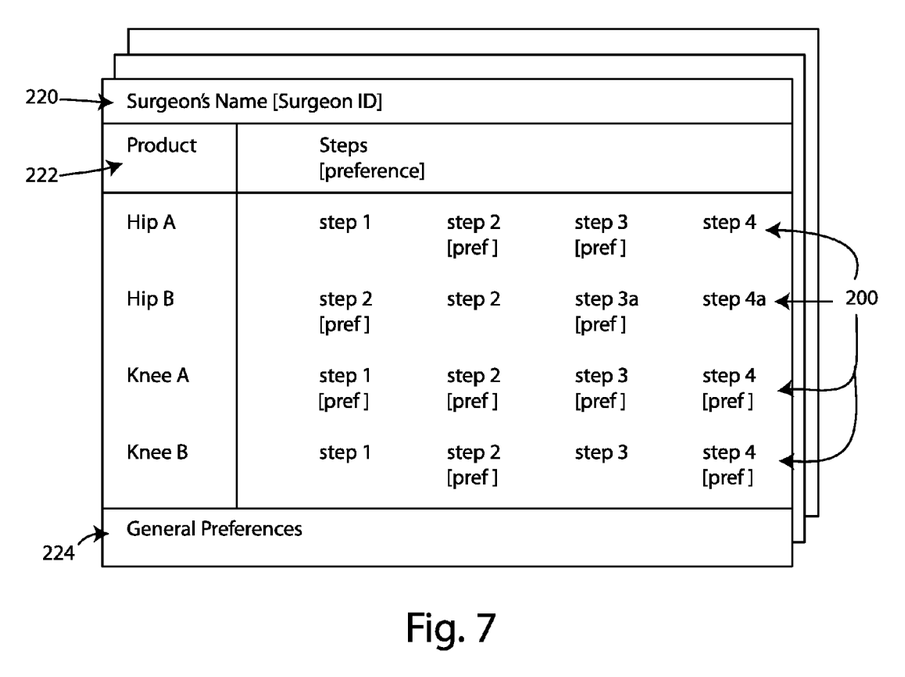
FIG. 7 is a data structure diagram summarizing how surgeon preferences may be compiled and organized as part of the joint replacement process.

The data structure of FIG. 5 may be represented in the computer-implemented database 120 as a collection of step sequences associated with each of the different prosthetic implants that are available for use by a given surgeon Such organization has been illustrated in FIG. 7. In FIG. 7, the data are arranged as complex records that each identify a particular surgeon, as at 220, and that further identify each of the different prosthetic implant devices that may be potentially selected for use by that surgeon, as at 222. Associated with each implant are a series of steps 200, with the surgeon's preference being also stored, if provided. In addition to the step-specific preferences, a set of general preferences 224 are also indicated for that surgeon. The data may be queried and sorted on a surgeon-by-surgeon basis, thus allowing a training regimen for a particular surgeon to be readily developed for use at step 94 (FIG. 4).

The data structures described in FIGS. 5 and 7 can be implemented as computer programming instructions in a variety of different ways. One preferred embodiment employs a relational database schema shown in FIG. 8. The schema employs five tables, a product table 250, a patient table 252, a surgeon table 254, a steps table 256 and a surgeon-specific table 258. The tables are joined by the relationships illustrated. Unless otherwise indicated, the relationships among tables are one-to-one relationships.

Figure 8:
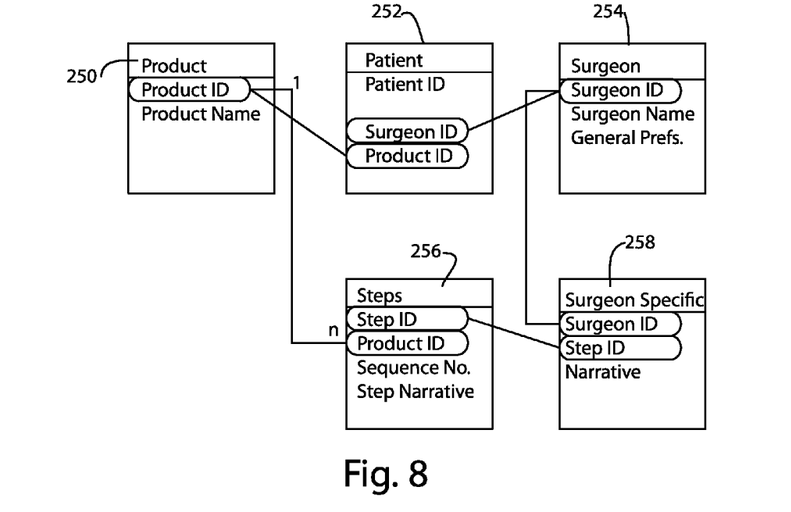
FIG. 8 is a database schema diagram illustrating one embodiment of a computer-implemented surgical team training management and scheduling system.

For any given patient (table 252), patient identification are stored along with identifiers indicating which surgeon is performing the surgery and which product is being installed. The product table is linked to the steps table so that for each product a plurality of steps may be associated. There is a one-to-many relationship between the product table 250 and the steps table 256. This is dictated by the fact that there are typically many steps performed to install a single product. The surgeon-specific table 258 stores a surgeon-specific narrative. The surgeon-specific table is related to the steps table so that for any given procedural step, a surgeon-specific narrative can be appended.

While the relational database embodiment of FIG. 8 represents one way to compile and store surgeon preference information, other embodiments are possible. By way of example, an alternate embodiment shown in FIG. 9 employs a spreadsheet software application to compile and store surgeon preference information. As illustrated, the spreadsheet software application is configured to display a main sheet 270, which has defined product column regions 272 devoted to each of a plurality of different prosthetic implant products. Product A and Product B are illustrated and it will be appreciated that the spreadsheet can extend laterally to accommodate additional product regions.

Figure 9:
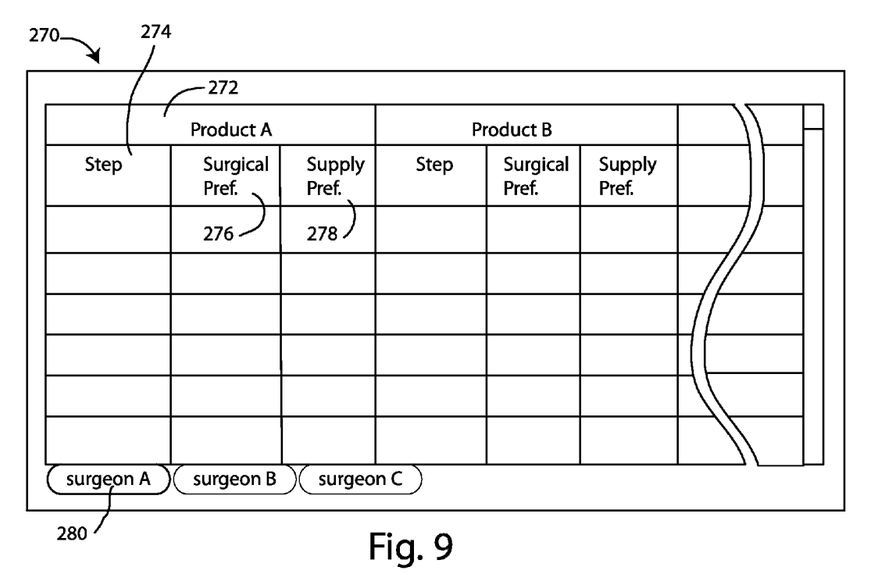
FIG. 9 is a spreadsheet diagram illustrating another embodiment of a computer-implemented surgical team training management system.

Each region is subdivided into individual columns representing implant installation steps 274, which can include pre-operative and post-operative steps, surgical preferences 276 and supply preferences 278. These surgical preferences 276 and supply preferences 278 define fields where surgeon specific preferences are entered and stored for each particular step. If the surgeon has no preference for a particular step, the associated surgical preference field and supply preference field may be left blank.

The individual installation steps are recorded, such as in chronological order, in the successive rows under the step 274 column. Thus the spreadsheet can show, at a glance, each step involved in the implantation process and what surgeon specific preferences have been recorded.

If desired, an additional set of columns may be added (not shown) listing each of the different surgical team member functions. Thus a column would be added for the surgical nurse, physician's assistant, and so forth. Where a particular team member may be called upon to assist in a given step, that step is flagged with an appropriate indicia (e.g., a predetermined character, such as 'X') in that member's column. These flags may be used to develop different views of the spreadsheet, such as using pivot tables, showing which surgeon specific preferences a given surgical team member must learn.

To accommodate the preferences of multiple surgeons, the spreadsheet 270 can be organized into multiple sheets, as depicted at 280. By selecting a given surgeon (surgeon A, surgeon B, surgeon C) at 280, the spreadsheet table for that surgeon's preferences will be displayed.

It will be understood that different spreadsheet arrangements are also possible. Thus, the example shown in FIG. 9 is intended merely to show how a spreadsheet implementation may be configured to compile and store surgeon preference information.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for performing orthopedic implant surgery comprising:
   supplying an orthopedic implant of a manufacturer to a surgeon for implantation into a patient;
   using a computer that is programmed with a data structure configured to separately store, for a given implant, (1) information identifying a plurality of surgical steps associated with preparing for and replacing or modifying the function of a joint bone or soft tissue associated with a joint selected from the group consisting of hip, knee, elbow, and shoulder, and associated with the implanting the given implant into the body of a patient, and (2) a preference attribute associated with each of said plurality of surgical steps in which to store information identifying a surgeon's preference with respect to the associated step;
   the manufacturer obtaining information prior to surgery about a particular surgeon's preferences in relation to the supplied implant and using said computer to create a specific record according to said data structure that is specific to the supplied implant and specific to the particular surgeon according to said data structure;
   the manufacturer populating the preference attributes of said specific record with information identifying the particular surgeon's preferences in relation to the steps associated with implanting the supplied implant;
   the manufacturer designating a surgical team member and using said computer and said specific record in training the designated surgical team member in the manner of implanting the supplied implant in accordance with the surgeon's preferences;
   the manufacturer supplying the services of the trained surgical team member together with the supplied implant; and
   the surgical team member performing procedures on the patient to assist the surgeon in implantation of the supplied implant, in accordance with the surgeon's preferences as reflected in the specific record stored in said programmed computer.

2. The method of claim 1 further comprising the manufacturer training a pre-operative team member in accordance with the surgeon's preferences and supplying the services of the pre-operative team member together with the supplied implant.

3. The method of claim 1 further comprising the manufacturer training a post-operative team member in accordance with the surgeon's preferences and supplying the services of the post-operative team member together with the supplied implant.

4. The method of claim 1 wherein the information obtained and compiled about the surgeon's preferences relate to the surgical techniques preferred by the surgeon in relation to the supplied implant.

5. The method of claim 1 wherein the information obtained and compiled about the surgeon's preferences relate to the surgical instruments preferred by the surgeon in relation to the supplied implant.

6. The method of claim 1 wherein the information obtained and compiled about the surgeon's preferences relate to the surgical supplies preferred by the surgeon in relation to the supplied implant.

7. The method of claim 1 further comprising:
the manufacturer obtaining custom information prior to surgery concerning the physical requirements of a custom implant and manufacturing a custom joint implant based on the obtained custom information; and
the manufacturer supplementing the training of surgical team member in the manner of implanting the custom implant.

8. The method of claim 1 wherein the supplied implant and the supplied services of the surgical team member are collectively supplied at a single bundled price comprising a materials component and a labor component.

9. The method of claim 1 wherein the step of compiling information from the surgeon prior to surgery comprises compiling and storing information about the surgeon's preferences in a database that relates a preference with an individual step of an implantation process associated with the supplied implant.

10. The method of claim 1 wherein the step of compiling information from the surgeon prior to surgery includes obtaining information observed during the step of training a surgical team member.

11. The method of claim 1 wherein the step of training a surgical team member includes placing the surgical team member in an observation situation to observe the surgeon performing an actual surgical procedure using a prosthetic implant substantially the same as the supplied implant.

12. The method of claim 1 wherein the step of training a surgical team member includes placing the surgical team member in a practice situation performing a simulated surgical procedure using a prosthetic implant substantially the same as the supplied implant.

13. The method of claim 1 wherein the step of training a surgical team member includes placing the surgical team member in a practice situation with the surgeon performing a simulated surgical procedure using a prosthetic implant substantially the same as the supplied implant.

14. The method of claim 1 further comprising:
the manufacturer providing supplies together with the supplied implant and the supplied services.

15. The method of claim 14 wherein the supplied implant, the supplied services of the surgical team member and the provided supplies are collectively supplied at a single bundled price comprising a materials component and a labor component.

16. A method for performing orthopedic implant surgery comprising:
supplying an orthopedic implant to a surgeon for implantation into a patient;
using a computer that is programmed with a data structure configured to separately store, for a given implant, (1) information identifying a plurality of surgical steps associated with preparing for and replacing or modifying the function of a joint bone or soft tissue associated with a joint selected from the group consisting of hip, knee, elbow, and shoulder, and associated with the implanting the given implant into the body of a patient, and (2) a preference attribute associated with each of said plurality of surgical steps in which to store information identifying a surgeon's preference with respect to the associated step;
obtaining information prior to surgery about a particular surgeon's preferences in relation to the supplied implant and using said computer to create a specific record according to said data structure that is specific to the supplied implant and specific to the particular surgeon according to said data structure;
populating the preference attributes of said specific record with information identifying the particular surgeon's preferences in relation to the steps associated with installing the supplied implant;
the supplier of the implant training a surgical team member using said computer and said specific record in training the designated surgical team member in the manner of implanting the supplied implant in accordance with the surgeon's surgical preferences based on the compiled information;
the supplier of the orthopedic implant supplying the services of the trained surgical team member together with the supplied implant; and
the surgical team member performing procedures on the patient to assist the surgeon in implantation of the supplied, in accordance with the surgeon's preferences as reflected in the specific record stored in said programmed computer.

17. The method of claim 16 further comprising the supplier training a pre-operative team member in accordance with the surgeon's preferences and supplying the services of the pre-operative team member together with the supplied implant.

18. The method of claim 16 further comprising the supplier training a post-operative team member in accordance with the surgeon's preferences and supplying the services of the post-operative team member together with the supplied implant.

19. The method of claim 16 wherein the information obtained and compiled about the surgeon's preferences relate to the surgical techniques preferred by the surgeon in relation to the supplied implant.

20. The method of claim 16 wherein the information obtained and compiled about the surgeon's preferences relate to the surgical instruments preferred by the surgeon in relation to the supplied implant.

21. The method of claim 16 wherein the information obtained and compiled about the surgeon's preferences relate to the surgical supplies preferred by the surgeon in relation to the supplied implant.

22. The method of claim 16 further comprising:
the supplier obtaining custom information from the surgeon prior to surgery concerning the physical requirements of a custom implant and supplying a custom joint implant based on the obtained custom information; and the supplier supplementing the training of surgical team member in the manner of implanting the custom implant.

23. The method of claim 16 wherein the supplied implant and the supplied services of the surgical team member are collectively supplied at a single bundled price comprising a materials component and a labor component.

24. The method of claim 16 wherein the step of compiling information from the surgeon prior to surgery comprises compiling and storing information about the surgeon's preferences in a database that relates a preference with an individual step of an implantation process associated with the supplied implant.

25. The method of claim 16 wherein the step of compiling information from the surgeon prior to surgery includes obtaining information observed during the step of training a surgical team member.

26. The method of claim 16 wherein the step of training a surgical team member includes placing the surgical team member in an observation situation to observe the surgeon performing an actual surgical procedure using a prosthetic implant substantially the same as the supplied implant.

27. The method of claim 16 wherein the step of training a surgical team member includes placing the surgical team member in a practice situation performing a simulated surgical procedure using a prosthetic implant substantially the same as the supplied implant.

28. The method of claim 16 wherein the step of training a surgical team member includes placing the surgical team member in a practice situation with the surgeon performing a simulated surgical procedure using a prosthetic implant substantially the same as the supplied implant.

29. The method of claim 16 further comprising:

the supplier providing supplies together with the supplied implant and the supplied services.

30. The method of claim 29 wherein the supplied implant, the supplied services of the surgical team member and the provided supplies are collectively supplied at a single bundled price comprising a materials component and a labor component.

* * * * *